United States Patent [19]

Robbins et al.

[11] Patent Number: 4,956,487
[45] Date of Patent: Sep. 11, 1990

[54] PROCESS FOR PRODUCTION OF THIOPHOSPHONATES

[75] Inventors: Jeffrey D. Robbins, Berkeley; Richard D. Gless, Jr., Oakland, both of Calif.

[73] Assignee: ICI Americas Inc., Wilmington, Del.

[21] Appl. No.: 283,345

[22] Filed: Dec. 12, 1988

[51] Int. Cl.$^5$ ............................................. C07F 9/40
[52] U.S. Cl. ........................................ 558/98; 558/83; 558/101
[58] Field of Search ............................ 558/83, 98, 101

[56] References Cited

U.S. PATENT DOCUMENTS

| | | | |
|---|---|---|---|
| 3,094,405 | 6/1963 | Toy et al. | 71/2.3 |
| 3,162,570 | 12/1964 | Wilson, Jr. | 514/141 |
| 3,790,649 | 2/1974 | Schumacher | 558/101 |
| 3,965,220 | 6/1976 | Schumacher et al. | 558/101 |
| 4,352,762 | 10/1982 | Fahmy | 558/98 |

FOREIGN PATENT DOCUMENTS

| | | |
|---|---|---|
| 239274 | 9/1987 | European Pat. Off. |
| 186464 | 10/1966 | U.S.S.R. |
| 187797 | 12/1966 | U.S.S.R. |
| 289096 | 12/1969 | U.S.S.R. |
| 197801 | 1/1978 | U.S.S.R. ............ 558/101 |
| 1049494 | 10/1983 | U.S.S.R. ............ 558/101 |

OTHER PUBLICATIONS

Nesterov et al., "Zh. Obshch. Khim., vol. 40," 1237 (1970), (English Translation).
Minich et al., CA 70:37096g: Izv-Akad. Nauk SSSR, Ser. Khim., 1792–1797, (1969).

Primary Examiner—Anton H. Sutto
Attorney, Agent, or Firm—Joel G. Ackerman

[57] ABSTRACT

Thiophosphonate compounds having the formula

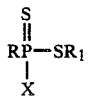

in which R is alkyl, haloalkyl or aryl; X is chloro or $SR_2$; $R_1$ is alkyl or aryl; and when X is $SR_2$ then $R_2$ is a group identical to $R_1$, or $R_1$ and $R_2$ taken together form an optionally alkyl-substituted polymethylene group, are prepared by reaction of a thiophosphonodichloride with a mercaptan in the presence of a catalytic amount of a quaternary ammonium or phosphonium salt, a tertiary amine or hydrohalide thereof or an alkali metal halide combined with a Crown ether, in the substantial absence of a base.

16 Claims, No Drawings

PROCESS FOR PRODUCTION OF THIOPHOSPHONATES

BACKGROUND AND PRIOR ART OF THE INVENTION

This invention relates to a process for production of thiophosphonates. In particular the invention relates to a process for production of thiophosphonates which in general have the formula $$\underset{X}{\overset{\overset{S}{\|}}{R\underset{|}{P}-SR_1}}$$

in which R is an alkyl, haloalkyl or aryl group; X is chloro or $SR_2$; $R_1$ is alkyl or aryl; and when X is $SR_2$ then $R_2$ is a group identical to $R_1$, or $R_1$ and $R_2$ taken together form an optionally alkyl-substituted polymethylene group. In the last mentioned case, the compounds have a cyclical structure. Preferred alkyl or haloalkyl groups for the above substituents are those containing from 1 to 8 carbon atoms. Examples include methyl, ethyl, n-propyl, isopropyl, the various butyl, pentyl, hexyl, heptyl and octyl groups, and halogenated alkyl groups of such types, for instance halomethyl such as chloromethyl. When $R_1$ and $R_2$ are combined, the group will be a polymethylene chain having from 2 to 4 methylene groups, optionally substituted by one or more $C_1$-$C_3$ alkyl groups. Examples of aryl groups are preferably phenyl and phenyl substituted by $C_1$-$C_4$ alkyl, $C_1$-$C_4$ alkoxy, halo, nitro, phenyl and/or phenoxy.

A number of different processes have been described for production of such compounds. In one process a thiophosphonodichloride is reacted with a mercaptan in the presence of a substantial amount of a hydrogen chloride acceptor or base. This reaction can be generally described as $$R-\overset{\overset{S}{\|}}{P}Cl_2 + 2R_1SH + 2\text{ (base)} \longrightarrow R-\overset{\overset{S}{\|}}{P}-(SR_1)_2 + 2\text{ base.HCl}$$

when $R_1$ (or $R_2$) is an alkyl or aryl group or $$R-\overset{\overset{S}{\|}}{P}Cl_2 + HS-(R_1+R_2)-SH + 2\text{ (base)} \longrightarrow$$

$$R-\overset{\overset{S}{\|}}{P}\begin{pmatrix} S+R_1 \\ + \\ S+R_2 \end{pmatrix} + 2\text{ base.HCl}$$

when $R_1+R_2$ form a polymethylene group (R is as described above). As can be seen from these reaction schemes, the base is normally used in an amount of 2 equivalents per equivalent of the thiophosphonodichloride. It is generally either a tertiary amine or an inorganic base, for instance, sodium hydroxide.

One such process is described in U.S. Pat. No. 3,094,405 of Toy et al. The preferred base is a tertiary amine. The reference also discloses that the reaction may be carried out in the absence of a base, although no such examples are included.

European Patent Application No. 239,274 of Sumitomo Chemical Co. discloses several processes for production of di-(tertiary butyl)alkyl phosphonotrithioates, one of which involves reaction of an alkyl thiophosphonodichloride with t-butyl mercaptan in the presence of stoichiometric quantities of aqueous sodium hydroxide, together with a quaternary salt catalyst and/or a copper catalyst.

U.S. Pat. No. 4,352,762 of Fahmy discloses production of a phosphonodithioic monohalide from the corresponding dihalide by reaction of only one equivalent of mercaptan and one equivalent of base.

USSR Patent No. 186,464 discloses production of what are termed trithiophosphinic acid esters by reaction of a thiophosphinic acid dichloride with two equivalents of a mercaptan in the presence of an amine salt of a polythiophosphoric or polythiophosphinic acid as catalyst. USSR Patent No. 187,797 discloses production of a phosphonothioic monohalide from the dihalide and one equivalent of a mercaptan in the presence of such a catalyst.

Other processes for production of compounds of this type include the two-step process of reacting a phosphinic dichloride with a mercaptan, followed by oxidation or sulfuration of the product (for instance, U.S. Pat. No. 3,162,570 of Wilson) by the reaction of an alkylthiophosphonodichloride with an alkali metal mercaptide (U.S. Pat. No. 4,752,604 of Chavdarian et al.), or by the reaction of a dithiophosphonic anhydride with a mercaptan (USSR Patent No. 289,096).

SUMMARY OF THE INVENTION

This invention comprises a process for production of thiophosphonates having the formula $$\underset{X}{\overset{\overset{S}{\|}}{R\underset{|}{P}-SR_1}}$$

in which R is alkyl, haloalkyl or aryl; X is chloro or $SR_2$; $R_1$ is alkyl or aryl; and when X is $SR_2$ then $R_2$ is a group identical to $R_1$; or $R_1$ and $R_2$ taken together form an optionally alkyl-substituted polymethylene group; comprising reacting a thiophosphonodichloride having the formula $$R-\overset{\overset{S}{\|}}{P}-Cl_2$$

with a mercaptan having the formula $R_1SH$ or $SH-(R_1+R_2)-SH$ if $R_1$ and $R_2$ taken together form a polymethylene group, in the presence of a catalytic amount of a member selected from the group consisting of (a) quaternary ammonium and phosphonium salts; (b) tertiary amines and hydrohalides thereof; and (c) an alkali metal halide in combination with a Crown ether, in the substantial absence of a base.

DETAILED DESCRIPTION OF THE INVENTION

This invention involves a process for the production of thiophosphonate compounds having the formula

in which R is aryl, alkyl or haloalkyl; X is chloro or $SR_2$; $R_1$ is alkyl or aryl; and when X is $SR_2$ then $R_2$ is a group identical to $R_1$; or $R_1$ and $R_2$ taken together form an optionally alkyl-substituted polymethylene group. The process involves the reaction of a thiophosphonodichloride having the formula

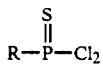

with an appropriate mercaptan in the presence of a catalyst as described below.

Aryl groups R, $R_1$ or $R_2$ are preferably phenyl or substituted phenyl in which the substituents are one or more of the following groups: $C_1$-$C_4$ alkyl, $C_1$-$C_4$ alkoxy, halo, nitro, phenyl, or phenoxy. For compounds in which R, $R_1$ or $R_2$ are alkyl or haloalkyl groups, the groups contain from 1 to 8 carbon atoms. Preferably $R_1$ and $R_2$ are $C_1$-$C_4$ alkyl. Examples of polymethylene groups $R_1+R_2$ are dimethylene (1,2-ethylene), trimethylene (1,3-propylene), tetramethylene (1,4-butylene) and alkyl-substituted chains such as

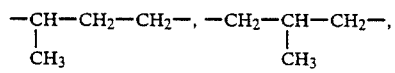

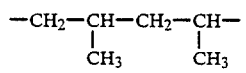

and the like. The polymethylene groups will contain from 2 to 12 carbon atoms. In one embodiment, $R_1$ and $R_2$ are identical tertiary alkyl groups, preferably tertiary butyl, and R is methyl or ethyl. In another embodiment, $R_1$ and $R_2$ are identical aryl groups. In yet another embodiment, X is halogen and $R_1$ is alkyl or aryl.

Prior art processes involving the reaction of a thiophosphonodihalide and a mercaptan were normally carried out in the presence of 1–2 equivalents of a base (usually a tertiary amine) per equivalent of the thiophosphonodichloride, producing a neutral compound (e.g., an amine hydrochloride) as a major by-product. If an inorganic base such as sodium hydroxide was used, the reaction was conducted in an aqueous or two-phase system, and the corresponding salt of that inorganic base was produced as a major by-product. The process of the present invention does not use such a base (whether amine or inorganic) and thus eliminates the production of major amounts of the salt by-product.

The process of this invention provides a means for producing compounds of the thiophosphonate type by this general reaction, using only a catalytic amount of a substance which may be one of three types: a quaternary ammonium or phosphonium salt, a tertiary amine or amine hydrohalide, or an alkali metal halide used in combination with a Crown ether.

The quaternary ammonium and phosphonium salt catalysts suitable for use in this invention have the general formula

in which Y is nitrogen or phosphorus; Z is an anion, preferably halogen or bisulfate; and $R_3$, $R_4$, $R_5$ and $R_6$ are independently aromatic, aliphatic, or aralkyl groups. Preferably the total number of carbon atoms in the quaternary onium cation is at least 12.

In these compounds "aralkyl" includes those groups normally denoted by that term, such as benzyl or phenethyl, but also includes a polymeric group derived from a substituted polystyrene-type ion exchange resin in which some of the aromatic groups of the polymer are linked to the nitrogen or phosphorus via a methylene group. In this last mentioned case, only one of the groups $R_3$–$R_6$ will be of the polystyrene resin type, with the others being lower alkyl such as methyl. Some suitable onium salt catalysts are tetrabutyl ammonium chloride, bromide and iodide, tetrabutyl phosphonium chloride and bromide, tetraethyl ammonium chloride, tetrabutyl ammonium bisulfate and tricaprylylmethyl ammonium chloride. Most preferred for this reaction are tetrabutyl ammonium and phosphonium halides.

The amines and hydrochlorides thereof suitable for use in this process are tertiary amines and include tertiary alkyl amines such as triethyl and tri-n-butyl amines, cyclical amines such as pyridine, mixed aromatic arophatic/aliphatic amines such as N,N-dimethylaniline and others, such as tris-[2-(2-methoxyethoxy)ethyl]amine, sold under the designation TDA-1 by the Rhone-Poulenc group of companies. For the third type of catalyst used in this process, the alkali metal halides are preferably potassium halides such as potassium chloride and potassium fluoride. These are used in combination with a Crown ether which is suitably selected for appropriate action together with the alkali metal halide. A preferred Crown ether for potassium halides is 18-Crown-6.

The process may be carried out in an organic solvent which is inert or non-reactive toward the reactants, catalysts and products and is preferably an aprotic non-polar solvent such as benzene, toluene, chlorobenzene, methylene chloride, hexane, and ethers such as dimethoxyethane and di-(n-butyl) ether. However, a solvent may not be needed, for instance when all reactants are in a single liquid phase.

The temperature of the process will depend on the reactants, product and solvent, if one is desired. In general, the process may be operated at a temperature of from about 0° C. to about 200° C., preferably from about room temperature (20° C.) to about 130° C. It is most effective to remove hydrogen chloride generated by the reaction as efficiently and quickly as possible. Preferably, therefore, the process is carried out under reflux temperature. The reflux temperature will be approximately that of the solvent, if a solvent is used. In cases in which the mercaptan is volatile, the reaction may be carried out with excess mercaptan, and the introduction of mercaptan may be controlled so as to maintain the system under reflux at the desired temperature.

The reaction may be conducted under atmospheric, subatmospheric, or superatmospheric pressure. It may be advantageous to utilize super- or subatmospheric pressures in order to provide reflux at a convenient reaction temperature.

In general the catalyst is used in an amount of from about 1 to about 10 mole percent, preferably from about 1 to about 5 mole percent, based on the starting thiophosphonodihalide.

In general the process tends to proceed stepwise, with the monochloro product (X=Cl) forming first, followed by further substitution to form the disubstituted product (X=SR$_2$). If the monochloro compound is desired, it can be advantageously obtained by monitoring or tracking the progress of the reaction with sampling and analysis, and stopping the reaction when formation of the disubstituted product becomes apparent. In general, the monochloro product also may predominate at slightly lower temperatures.

The process of this invention is further illustrated by the following examples.

EXAMPLE 1

Preparation of Ethylene phenyltrithiophosphonate

This example illustrates the production of a compound in which R$_1$ and R$_2$ taken together are an alkylene, particularly ethylene, group.

There were placed in a flask 1.81 grams (g) (5.3 mmol) tetrabutylphosphonium bromide, 1.32 g n-octadecane (internal standard for gas chromatography), 15.8 milliliters (mL) (21.5 g, 98.6 mmol) phenylphosphonothioic dichloride (97% purity) and 50 mL benzene. The contents of the flask were heated to reflux and then there was added over a time of 0.2 hours a solution of 1.7 mL (1.9 g, 20 mmol) of 1,2-ethanedithiol (96%) in 10 mL benzene. After a further 0.9 hours at reflux temperature, analysis by gas chromatography indicated that a reaction had begun and then slowed appreciably. Then, a further 7.0 mL of the ethanedithiol solution (7.9 g, 80 mmol) was added over 0.1 hour at reflux and the resulting solution then heated at reflux (89°–92° C.) for 5.6 hours. At the end of this time, gas chromatographic analysis indicated greater than 99% conversion of the starting phenylphosphonothioic dichloride.

The reaction mixture was cooled, washed with water, dried and concentrated in vacuo to give 22.8 g of an oil which crystallized on storage at 0° C. Recrystallization of the crude product from ether provided 12.5 g (54% of theoretical yield) of colorless prisms, m.p. 67°–71° C. which was identified by spectroscopic analysis as the desired product.

COMPARATIVE EXAMPLE 1

The reaction was carried out as in Example 1 but with no tetrabutylphosphonium bromide present. After the same time period, gas chromatographic analysis indicated that the conversion of phenylphosphonothioic dichloride was less than 10% and the yield of desired product ethylene phenyl trithiophosphonate was less than 5%.

EXAMPLE 2

Preparation of S,S-Di-(tertiary butyl)methylphosphonotrithioate

In a flask were placed 8.5 g (0.035-mol) tetrabutylphosphonium bromide (98 wt. %) and 77.3 g (0.513 mol) methylphosphonothioic dichloride (98.9%). The flask was then heated to 110° C. to produce a clear solution. Then, tertiary butyl mercaptan was added until refluxing began at a reaction temperature of 106° C. and thereafter the mercaptan was added at a rate so as to maintain the reflux at a reaction temperature of 100°–110° C. while the reaction was monitored by gas chromatography. At the end of 13.6 hours, the area percent ratio of desired product to intermediate monochloride was 93:2 with the total amount of tertiary butyl mercaptan having been charged at 150.9 g (1.67 mol, 326 mole %). The reaction mixture was then cooled. There was obtained 157.4 g of the desired product (65.3 wt. % purity, 0.401 mol, 78.1% corrected yield), a clear yellow oil.

COMPARATIVE EXAMPLE 2

The procedure of Example 2 above was repeated, using 0.1 mol methylphosphonothioic dichloride, but without the inclusion of tetrabutylphosphonium bromide. A total of 70 mmol tertiary butyl mercaptan was added to maintain reflux at 104°–110° C. over a period of 4.5 hours. Analysis of the product mixture indicated less than 1% yield of the desired product, 1% yield of intermediate monochloride, and 84% recovery of unreacted dichloride.

EXAMPLES 3–16

The following examples demonstrate production of S,S-di-(tertiary butyl)methylphosphonotrithioate by reaction of methylphosphonothioic dichloride and tertiary butyl mercaptan using various other catalysts within the scope of this invention.

In general, the procedure of these examples was carried out as follows: In a flask were placed 14.9 g (0.1 mol) methylphosphonothioic dichloride and 0.005 mol of the indicated catalyst. The reaction mixture was then heated to 100°–110° C. Then, tertiary butyl mercaptan was added until refluxing began, and was thereafter added at a rate to maintain to reflux at the reaction temperature indicated in the following table. The reaction was monitored by gas chromatography. At the end of the time indicated in the table below, the desired product was obtained with the yield as indicated. Analysis was also carried out by gas chromatography for the yield of intermediate product S-(tertiary butyl)methylphosphonodithioic monochloride.

Results are shown in the following table.

TABLE

| Ex. | Catalyst | t-Butyl Mercaptan mole % | Time, hr | Temp. °C. | Product Yield (% Theo.) | Product Purity % | Monochloride Yield % |
|---|---|---|---|---|---|---|---|
| 3 | (n-C$_4$H$_9$)$_4$N$^+$I$^-$ | 528 | 9.5 | 102–106 | 82.9 | nd* | 5 |
| 4 | (n-C$_4$H$_9$)$_4$N$^+$Cl$^-$ | 453 | 9.5 | 102–110 | 82.1 | nd | 4 |
| 5 | Aliquat ® 336$^1$ | 414 | 9.7 | 102–110 | 67.7 | 78.4 | 6 |
| 6 | (n-C$_4$H$_9$)$_4$N$^+$HSO$_4^-$ | 484 | 17.3 | 100–110 | 44.7 | nd | 9 |
| 7 | (C$_2$H$_5$)$_4$N$^+$Cl$^-$ | 440 | 12.0 | 102–110 | 68.4 | 84.0 | 2 |
| 8 | "ion exchange" quaternary salt$^2$ | 489 | 17.0 | 100–100 | 32.6 | nd | 1 |
| 9 | (n-C$_4$H$_9$)$_4$P$^+$Br$^-$ | 461 | 15.3 | 104–108 | 85.7 | nd* | 0 |
| 10 | "ion exchange" quaternary salt$^3$ | 360 | 12.7 | 102–110 | 47.8 | nd | 6 |

TABLE-continued

| Ex. | Catalyst | t-Butyl Mercaptan mole % | Time, hr | Temp. °C. | Product Yield (% Theo.) | Product Purity % | Monochloride Yield % |
|---|---|---|---|---|---|---|---|
| 11 | $(C_2H_5)_3NH^+Cl^-$ | 461 | 8.7 | 118-125 | 46.2 | 65.3 | 1.0 |
| 12 | 2,6-lutidine | 505 | 19.0 | 90-110 | 27.3 | nd | 17 |
| 13 | N,N-dimethylaniline | 396 | 12.8 | 100-110 | 55.2 | 67.0 | 13 |
| 14 | "Alamine"[4] | 434 | 13.7 | 95-110 | 59.6 | nd | 10 |
| 15 | KCl/18-Crown-6 | 447 | 11.1 | 100-110 | 52.0 | 0 | 10 |
| 16 | KF/18-Crown-6 | 281 | 5.8 | 100-110 | 34.9 | nd | 28 |

*Not determined because material separated into 2 phases.
[1]Methyltricaprylyl ammonium chloride, formula $CH_3(C_{8-10}H_{18-22})N^+Cl^-$.
[2]Trimethyl mono-polystyrene type ammonium quaternary salt (chloride) prepared from AG-MP1 ion exchange resin obtained from Bio-Rad, Inc., Hercules, California.
[3]Tri-(n-butyl) mono-polystyrene type quaternary salt (chloride) prepared from tri-(n-butyl)phosphine and 2% cross-linked Merrifield resin obtained from Aldrich Chemical Co., Milwaukee, Wisconsin. (See Cinquini et al., J. Chem. Soc., Chem. Comm., 394 (1976)).
[4]Mixture of trialkylamines, average molecular weight 342, obtained from Henkel Corp.

EXAMPLE 17

Preparation of S,S-Diphenylmethylphosphonotrithioate

This example illustrates the preparation of a compound in which $R_1$ and $R_2$ are aryl groups.

There were placed in a flask 7.57 g (0.051 mol) methylphosphonothioic dichloride, 22.3 g toluene (solvent), and 0.77 g (0.0022 mol) tetra-(n-butyl)phosphonium bromide. The temperature was raised from 24° C. (room temperature) to 107° C., at which time the mixture began refluxing. At this point, addition of thiophenol was commenced (total 18.5 mL, 0.155 mol), dropwise. The reaction was carried out for 2.75 hours, with dropwise addition of thiophenol and heating to maintain the mixture under reflux. At the end of that time, the reaction mixture was diluted with 50 mL diethyl ether, washed with water (3 portions, 50 mL each) and then washed with 1N sodium hydroxide (3 portions, 50 mL each). Solvent was removed on a rotary evaporator, producing 8.49 g (56% of theoretical yield) of a yellow oil, which was identified spectroscopically as the desired compound.

EXAMPLE 18

Preparation of S-(n-Butyl)ethylphosphonodithioic chloride

There were placed in a flask 0.82 g (0.0024 mol) tetra-(n-butyl)phosphonium bromide and 8.98 g (0.0542 mol) ethylphosphonothioic dichloride. The temperature was then raised from room temperature to about 110° C., at which point addition of 1-butanethiol commenced. The reaction was carried out at reflux for 2 hours at 100°-110° C. with a total of 50 mL (0.46 mol) 1-butanethiol having been introduced.

The reaction mixture was cooled, then stripped on a rotary evaporator for 2 hours under vacuum and at a temperature of 40° C. There was obtained 13.14 g of a gold-colored oil which was dissolved in diethyl ether and washed with portions of 10% sodium carbonate solution and water. The phases were then separated, and the organic phase was dried. The dried material was again stripped on a rotary evaporator; there was obtained 10.85 g (92.5% of theoretical yield) of a yellow oil, identified spectroscopically as the monochloride product.

COMPARATIVE EXAMPLE 3

The procedure of Example 18 above was repeated, using 9.0 g (0.054 mol) ethylphosphonothioic dichloride and 7 mL (0.06 mol) 1-butanethiol, but without the inclusion of tetrabutylphosphonium bromide. The reaction mixture was heated for a total of 4 hours at 126° C. Analysis of the product mixture after this time indicated 2.7 area % of the desired product, 4.4 area % of the S,S-(di-n-butyl) compound, 1.9 area % of tri-(n-butyl)-tetrathiophosphate and 88.1 area % of unreacted phosphonothioic dichloride.

EXAMPLE 19

Preparation of S,S-di(n-butyl)ethylphosphonotrithioate

This example illustrates the production of the above compound through the monochloride intermediate which was separately produced in Example 18, and illustrates the step-wise nature of this reaction.

There were placed in a flask 9.36 g (0.0566 mol) ethylphosphonothioic dichloride and 0.82 g (2.34 mmol) tetra(n-butyl)phosphonium bromide. The temperature was raised to 120° C., at which point addition of n-butyl mercaptan was commenced. The reaction was carried out for approximately 8 hours with controlled addition of the mercaptan and heating to maintain the mixture under reflux. A total of 21 mL (0.0194 mol) of n-butyl mercaptan was used in this procedure.

The reaction was monitored by gas chromatography with sampling at various intervals to track the progress. This monitoring clearly showed that the reaction proceeded through formation of the phosphonodithioic chloride (product of Example 18) and further conversion of it to the phosphonotrithioate.

By way of example, gas chromatographic analysis of a sample obtained after 10 minutes showed the reaction mixture contained approximately 63 area % unreacted phosphonothioic dichloride and approximately 33.5% S-(n-butyl)ethylphosphonodithoic chloride. A sample removed after approximately 1 hour, 25 minutes, showed the reaction mixture contained approximately 63.1 area % of the monochloride and approximately 27.9 area % of the desired phosphonotrithioate product. Near the end of the run, the sample indicated the reaction mixture contained approximately 93.55 area % of the desired product and approximately 1.6 area % of the monochloride.

The reaction mixture was stripped for 2 hours on a rotary evaporator, yielding 12.71 g of a pale yellow liquid which was determined by spectroscopic analysis to be the desired product (83% of theoretical yield). To remove the residual catalyst, the product was then dissolved in methylene chloride, washed with aqueous 2N HCl, dried and solvent stripped. There was obtained 6.87 g (59.7% of theoretical yield) of a pale yellow liquid, identified spectroscopically as the desired product.

What is claimed is:

1. A process for production of thiophosphonate compounds having the formula

in which R is alkyl, haloalkyl or aryl; X is chloro or $SR_2$; $R_1$ is alkyl or aryl; and when X is $SH_2$ then $R_2$ is a group identical to $R_1$, or $R_1$ and $R_2$ taken together form an optionally alkyl-substituted polymethylene group, comprising reacting a thiophosphonodichloride having the formula

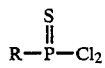

with a mercaptan having the formula $R_1SH$, or $HS-(R_1+R_2)-SH$ when $R_1$ and $R_2$ taken together form a polymethylene group, in the presence of a catalytic amount of a member selected from the group consisting of (a) quaternary ammonium or phosphonium salts having the general formula $R_3R_4R_5R_6Y^+Z^-$ in which Y is nitrogen or phosphorus, Z is an anion, and $R_3$, $R_4$, $R_5$, and $R_6$ are independently aromatic, aliphatic or aralkyl groups, the total number of carbon atoms in the quaternary onium cation being at least twelve; and (b) an alkali metal halide in combination with a Crown ether, in the substantial absence of a base.

2. A process according to claim 1 in which X is $SR_2$ and $R_1$ and $R_2$ are identical alkyl groups.

3. A process according to claim 2 in which $R_1$ and $R_2$ are identical tertiary alkyl groups.

4. A process according to claim 1 in which R is $C_1-C_4$ alkyl and $R_1$ and $R_2$ are both tertiary butyl.

5. A process according to claim 1 in which X is $SR_2$ and $R_1$ and $R_2$ are identical aryl groups.

6. A process according to claim 5 in which $R_1$ and $R_2$ are phenyl or substituted phenyl.

7. A process according to claim 1 in which R is phenyl.

8. A process according to claim 1 in which X is chloro.

9. A process according to claim 8 in which R and $R_1$ are $C_1-C_4$ alkyl.

10. A process according to claim 1 in which the catalyst is a quaternary ammonium or phosphonium salt.

11. A process according to claim 10 in which the catalyst is a quaternary ammonium or phosphonium halide.

12. A process according to claim 1 in which the catalyst is used in an amount of from about 1 to about 10 mole percent based on the thiophosphonodichloride.

13. A process according to claim 1 in which the reaction is conducted in the presence of an inert organic solvent.

14. A process according to claim 1 in which the reaction is conducted in the absence of a solvent.

15. A process according to claim 1 in which the catalyst is a quaternary phosphonium salt.

16. A process according to claim 15 in which the catalyst is a quaternary phosphonium halide.

* * * * *

UNITED STATES PATENT AND TRADEMARK OFFICE
CERTIFICATE OF CORRECTION

PATENT NO. : 4,956,487
DATED : September 11, 1990
INVENTOR(S) : Jeffrey D. Robbins and Richard D. Gless, Jr.

It is certified that error appears in the above-indentified patent and that said Letters Patent is hereby corrected as shown below:

In Column 9, line 13, "$SH_2$" should read --$SR_2$--.

Signed and Sealed this

Fifth Day of April, 1994

*Attest:*

BRUCE LEHMAN

*Attesting Officer*  *Commissioner of Patents and Trademarks*